United States Patent [19]

Newton et al.

[11] 4,420,720
[45] Dec. 13, 1983

[54] FIELD FOCUSED PARTICLE SENSING ZONE

[75] Inventors: William A. Newton, Dade County, Fla.; Marshall D. Graham, Framingham, Mass.

[73] Assignee: Coulter Electronics, Inc., Hialeah, Fla.

[21] Appl. No.: 279,920

[22] Filed: Jun. 29, 1981

[51] Int. Cl.³ .......................................... G01N 27/00
[52] U.S. Cl. ................................ 324/71.4; 324/71.1; 324/71.3; 377/11
[58] Field of Search ..................... 377/10–12; 324/71.1, 71.3, 71.4

[56] References Cited

U.S. PATENT DOCUMENTS

| | | | |
|---|---|---|---|
| 2,649,573 | 8/1953 | Goldberg | 324/71.1 |
| 2,667,159 | 1/1954 | Goldberg | 324/71.1 |
| 2,683,986 | 7/1954 | Bartlett | 324/71.4 |
| 3,560,847 | 2/1971 | Boyd | 324/71.1 |
| 3,853,750 | 12/1974 | Volsg | 324/71.4 |
| 3,863,159 | 1/1975 | Coulter | 377/11 |
| 4,298,836 | 11/1981 | Groves | 324/71.3 |

Primary Examiner—Michael J. Tokar
Attorney, Agent, or Firm—Gerald R. Hibnick; William A. Newton

[57] ABSTRACT

A particle analyzer wherein a flow of liquid suspension, having individually entrained particles, flows along a predetermined path; a center pair of electrodes are positioned on opposed sides of the predetermined path: the center electrodes are energized to provide an electrical sensing field therebetween, two pairs of outer electrodes are positioned so that one pair is on each side of the center electrodes; the outer electrodes are oriented and/or energized so that their electrical fields bulge outward in the direction of the sensing field of the center plates to narrow the width of the sensing field along the predetermined path. Additionally, the field between the center plates can be focused in additional directions and the sensing electrode arrangement can be implemented in a flow cell, with or without an aperture, or on the surface of a substrate.

28 Claims, 11 Drawing Figures

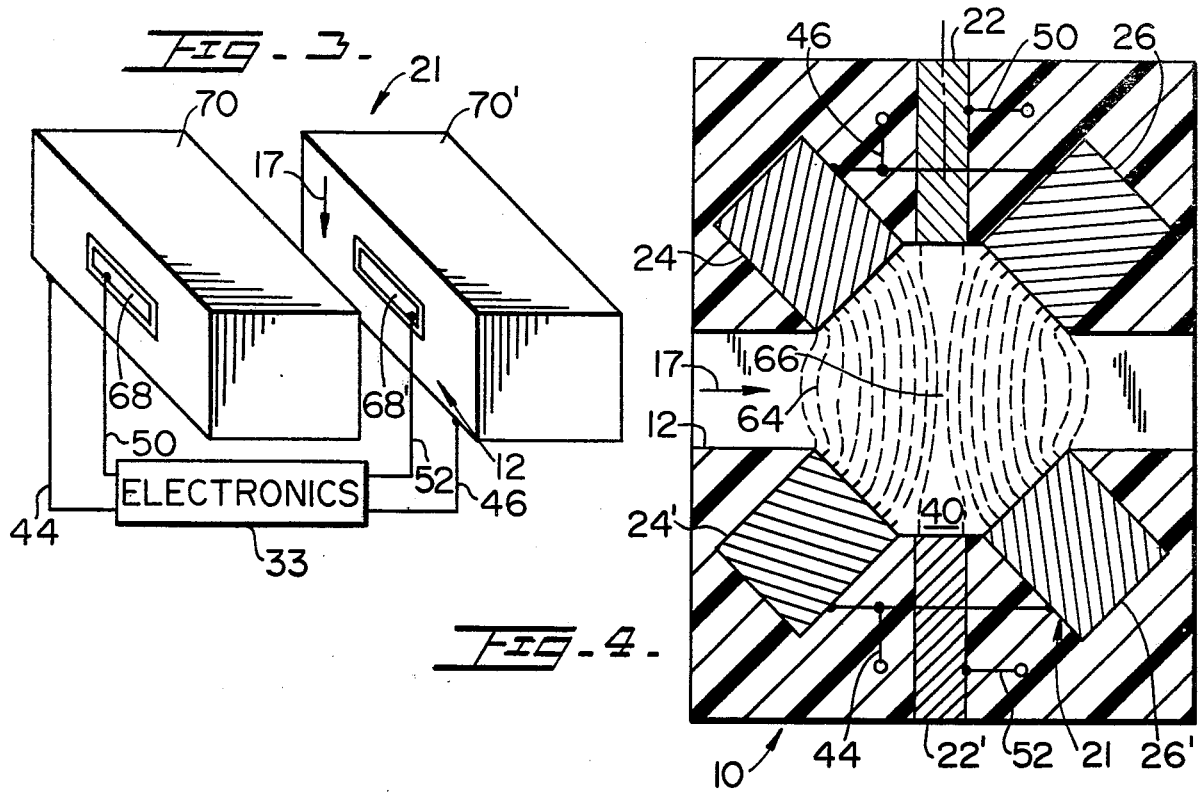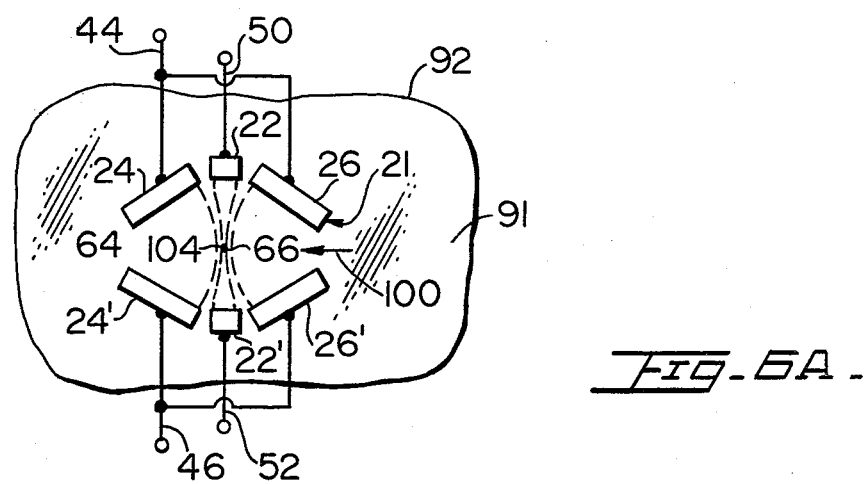

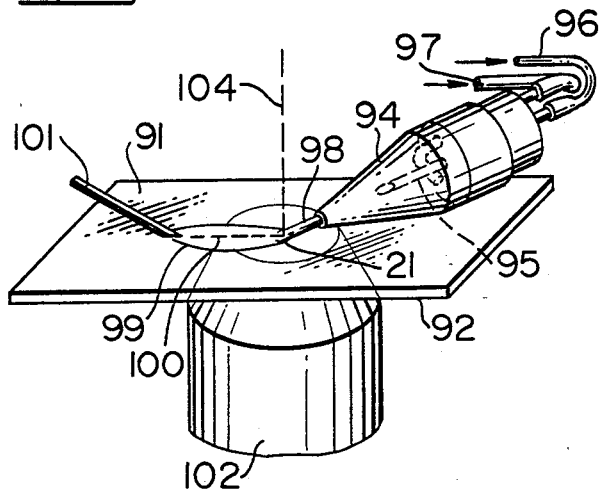
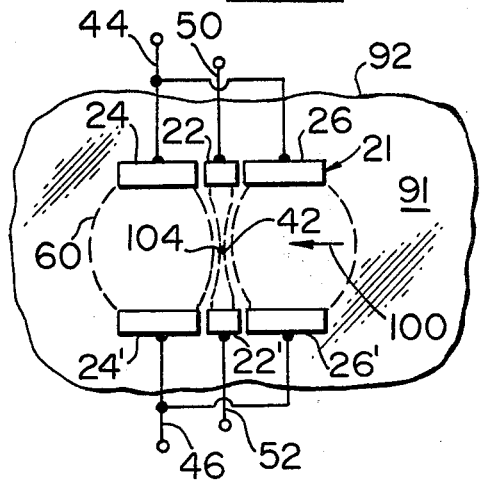
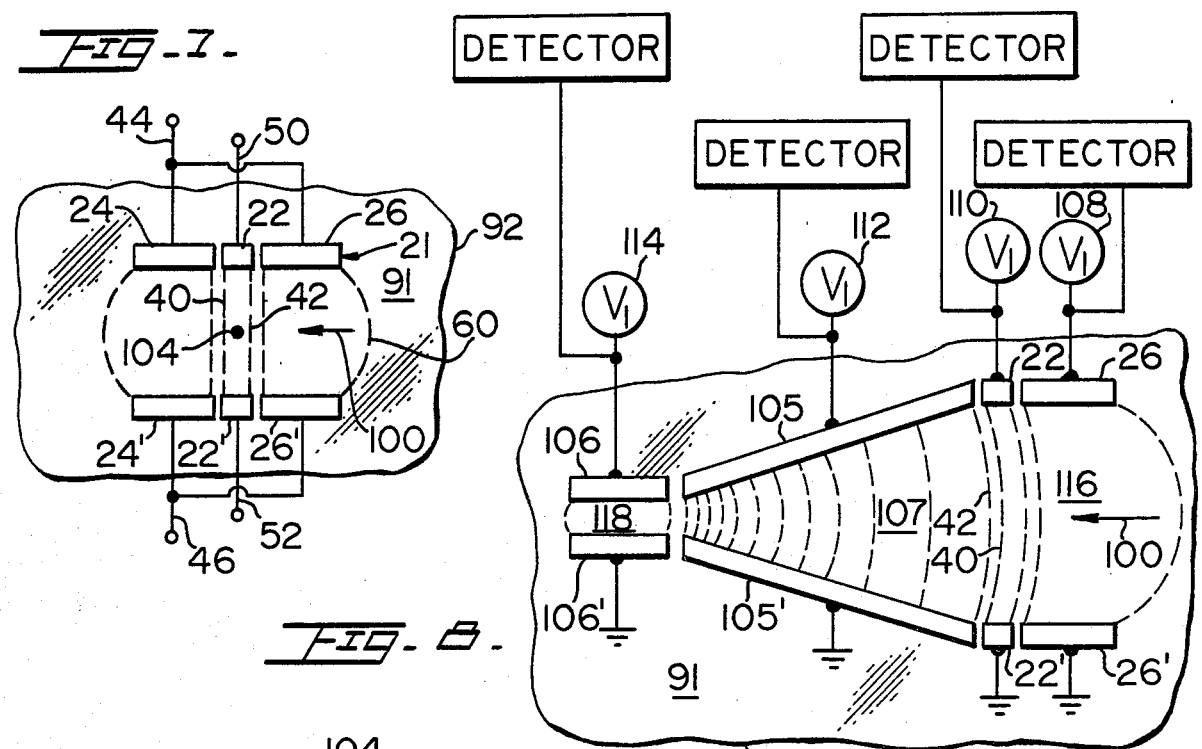

FIELD FOCUSED PARTICLE SENSING ZONE

FIELD OF THE INVENTION

The present invention relates to electrical volume sensing particle analyzers using the principle of Wallace Coulter for counting, sizing, and analyzing particles suspended in a liquid suspension.

BACKGROUND OF THE INVENTION

Since its conception more than 27 years ago, the principle of particle counting and sizing invented by Wallace H. Coulter has resulted in numerous methods and apparatuses for the electronic counting, sizing and analysis of microscopic particles, which are scanned in a fluid suspension, as shown by the pioneer U.S. Pat. No. 2,656,508 to Coulter. In this prior art particle analyzer, a D.C. electric current flow is established between two vessels by suspending electrodes in the respective bodies of the suspension fluid. The only fluid connection between the two bodies is through an orifice; hence, an electric current flow and field are established in the orifice. The orifice and the resultant electric field in and around it constitute a sensing zone. As each particle passes through the sensing zone, for the duration of the passage, the impedance of the contents of the sensing zone will change, thereby modulating the current flow and electric field in the sensing zone, and hence causing the generation of a signal to be applied to a detector suitably arranged to respond to such change. (The mark "Coulter" is a registered trademark, Registration No. 995,825, of Coulter Electronics, Inc. of Hialeah, Fla.)

In the commercial apparatus constructed in accordance with the heretofore mentioned U.S. Pat. No. 2,656,508, field excitation has been supplied by a direct current or low frequency source. The electrical change, i.e., D.C. signal, caused by the passage of a particle through the electric field of small dimensions, excited by a direct or low frequency current, is approximately proportional to particle size. A direct current is considered to be of zero frequency in this application. However, the impedance sensing principle has been materially expanded to provide information concerning particles being studied, not limited only to characteristics due to the size of particles, but including characteristics due to the composition and nature of the material constituting the particles, as disclosed in U.S. Pat. No. 3,502,974 to Coulter et al and U.S. Pat. No. 3,502,973 to Coulter et al. These prior art apparatuses generally have at least two current sources, both of which are applied to the sensing zone simultaneously, one having a radio frequency (RF) and the other being the previously described "zero frequency" direct current (DC) or, alternatively, having a sufficiently low frequency that the reactive part of the particle impedance has a negligible effect on the response of the apparatus. One of the useful particle descriptors that can be obtained from this dual source arrangement is the "internal conductivity" or "opacity" of the particles. More specifically, with biological cells, their membranes have a very high resistivity in the range of a dielectric; however, the internal portion of the cell is fairly conductive. The RF current passes through the cell's membrane, thereby generating a detectable RF signal which correlates to the "internal conductance" for each particle. When the D.C. size signal for a cell is divided into the RF signal for that cell, a measurement correlating with the "internal conductivity" of the cell is obtained.

The drawback of the above described particle analyzers is that the size and internal conductivity measurements generally do not correlate exactly with the actual or true volume and internal conductivity, respectively, of the cell. Generally, due to the hydrodynamic focusing in most apparatuses, elongated particles will be aligned with their elongated axis substantially parallel to the center axis of the orifice. With two equal volume particles, one being spherical and one being elongated, the spherical particle, while passing through the orifice, will have a greater cross section perpendicular to the current flow than the elongated particle. Hence, the spherical particle will distort the field in such a manner that it will give a greater measured size signal than the elongated particle, despite their equal volumes. Consequently, particles have been classified as to their shape by a term called "shape factor" which is used to correct their measured D.C. size signal. For instance, if an extremely elongated particle is assigned a shape factor of 1.0, then the spherical particle of the same volume has a shape factor of 1.5.

To correct for the inaccuracies introduced into the measured parameters by the particle's shape, the shape factor can be accurately measured on a cell by cell basis by obtaining a third signal, such as length, in addition to the RF and DC signals and then correcting the measured parameters to obtain accurate values, as described in allowed U.S. patent application No. 096,945, filed Nov. 23, 1979, to Groves et al. Now U.S. Pat. No. 4,298,836. However, this arrangement has the disadvantage of requiring an optical source and detector for obtaining the required length by making a "time of flight" measurement.

A second drawback of the prior art electronic volume sensing particle analyzers is that slit scanning of the individual cell cannot be accomplished, such scanning being possible only with optical particle analyzers, as shown in U.S. Pat. No. 3,657,537 to Wheeless. More specifically, with the optical particle analyzers, a narrow illuminating beam, having a width less than the length of the cell traversing the same, excites fluorescence from a stained cell. In this manner the internal constituents of the cell are examined, such as the relative sizes of the cell's nucleus and cytoplasm. It is known that there are differences in internal resistivities of different portions of the cell, such as, for example, between the nucleus and the surrounding cytoplasm. However, in these prior art analyzers, these internal differences have not been measureable or subject to being quantified, due to the sensing zone created by the electric field being always much longer in length than the cell. For instance, a sensing zone in a 100 micron long aperture will be substantially longer than the 100 microns and will typically receive cells having lengths in the range of 10 microns.

A third drawback of the prior art electronic volume sensing analyzers is that the volume of the sensing zone is much greater than the volume of a cell, resulting in some loss in signal resolution. For instance, the smallest practical orifice size would have a cross-sectional diameter of 50 microns and a length of 50 microns, as compared to the 10 micron diameter of the cell, resulting in a volume 187 times greater than the cell. The ratio of the volumes of the actual sensing zone and the cell is even greater.

A fourth drawback of the electronic volume particle analyzers of the prior art is that in order for microscopic sized particles to be analyzed, the aperture must form a constricted passageway for the electrical current, generally having a diameter no greater than 50 to 100 microns to create sufficient current densities. These microscopic dimensions make difficult the fabrication of the aperture within reasonable tolerances and in operation frequently lead to the aperture becoming clogged with debris.

In U.S. Pat. No. 3,821,644 to Gohde et al. an electrode arrangement is shown for creating a unidirectional electric sensing field between plates for making the detected signals insensitive to particle trajectories. More specifically, each particle is forced to traverse or cut the same amount of current, regardless of the displacement of the particle's trajectory from the center axis of the orifice, due to the field being unidirectional. The width of this sensing field is limited by how thin the center electrodes can be made, which is generally in excess of 100 microns. As taught by this patent, the sensing zone is much longer in length than the cell; hence, the peak amplitude of the signal occurs when the entire cell is within the confines of the sensing zone.

The previously mentioned U.S. Pat. Nos. 3,502,974, 3,502,973 and 4,298,836 are incorporated herein by specific reference thereto.

SUMMARY OF THE INVENTION

The present invention is directed toward a particle analyzer apparatus comprising means for providing a flow of liquid suspension, having individual particles entrained therein, along a predetermined path; a first pair of plates positioned on opposed sides of the predetermined path; first energizing means for providing an electrical sensing field extending from one of the first plates through the liquid suspension to the other first plate; and two pairs of outer plates, a second pair and a third pair, positioned on opposite sides of the first pair of plates, ech of the second and third pair of plates having their plates positioned on opposed sides of the predetermined path. The second and third pairs of plates are electrically energized and/or angled with respect to the sensing field so as to narrow the width of the sensing field along the predetermined path to a dimension substantially less than the length of a given particle passing therethrough. When the first and second energizing means generate a field with an RF frequency, then the membranes of biological cells are shunted so that the sensing field scans a continuously changing portion of the internal constituents of the given particle, so as not to scan the total particle at any given time. In addition to or instead of the R.F. energization of the plates, the plates can be energized at a zero or low frequency to give length, size, and shape measurements for the particle.

The narrowing of the sensing field can be accomplished by making the adjacent fields of the outer plates stronger than the field of the center plates and/or the outer plates can be positioned so that their remote ends are angled toward the predetermined path, causing the fields of the outer plates to bulge toward and narrow the sensing field of the center plates. In addition to narrowing the sensing field of the center plates in a direction parallel to the flow of the particles along the predetermined path, the sensing field can also be focused in a second direction which is perpendicular to the predetermined path. The sensing arrangement can be implemented in a flow cell or, alternatively, on the surface of a single substrate. When etched in a substrate, the sensing electrode arrangement can readily take a plurality of different forms, one of which can be used to examine the cell breakdown process that occurs with an increasing voltage gradient.

In the above-described arrangement, the fields of the outer plates are of a sufficient strength to narrow the width of the sensing zone to be a fraction of the length of particles being analyzed so as to undertake electrical slit scanning of the particle. Additionally, the scope of the present invention is intended to cover any focused electrical field arrangement implemented on the surface of a single substrate for the purposes of confining the width of the electrical sensing field along the predetermined path. The confinement or focusing of the sensing field by the fields of the outer plates allows for the center plates to be sufficiently spaced-apart so as to cause the sensing current, which takes a curved path to and from the substrate, to have a relatively uniform current density in the cross section of the liquid suspension, taken in a plane which is perpendicular to the substrate and which passes through the predetermined path. This spacing of the center plates becomes feasible because the confinement of the width of the sensing field, which would normally bulge outward, increases the magnitude of the current density and narrows the width of the particle sensing region, thereby giving acceptable particle pulse resolution and particle throughput.

As described above, the electrode sensing arrangement embodying the invention makes possible the implementation of an electrical sensing field on a single substrate, such substrate having a thin liquid layer therein containing the liquid suspension. Secondly, when the electrode sensing arrangement is implemented on a single substrate, alignment problems between the electrodes of each pair are eliminated, in that the electrodes can be accurately etched into the surface of the substrate in a fixed relationship. Moreover, the greater the focusing of the sensing field, the larger the center electrodes and the spacing therebetween can be made, making their fabrication easier.

BRIEF DESCRIPTION OF THE DRAWINGS

Further objects and advantages of the present invention will become apparent as the following description proceeds, taken in conjunction with the accompanying drawings in which:

FIG. 3 shows an alternative embodiment of the sensing electrode arrangement wherein the sensing field is focused in two directions;

FIG. 4 is a cross-sectional view of an alternative embodiment of the sensing electrode arrangement incorporating the present inventions;

FIG. 5 shows the sensing electrode arrangements embodying the present invention implemented on the surface of a substrate;

FIG. 6 shows an enlarged, fragmentary top view of the electrode arrangement as implemented on the surface of the slide;

FIG. 6A shows an alternative embodiment of the sensing electrode arrangement as implemented on the slide;

FIG. 7 shows an alternative embodiment of the sensing electrode arrangement as implemented on the slide;

FIG. 8 shows another alternative embodiment of the sensing electrode arrangement as implemented on the surface of the slide;

FIG. 9 shows a cross-sectional view of the sensing electrode arrangement implemented on a slide with a cover slide thereover defining a flow chamber therebetween; and FIG. 10 shows a cross-sectional view of the embodiment shown in FIG. 9 taken along section line 10—10.

DETAILED DESCRIPTION OF THE PREFERRED EMBODIMENTS

Figure 1:
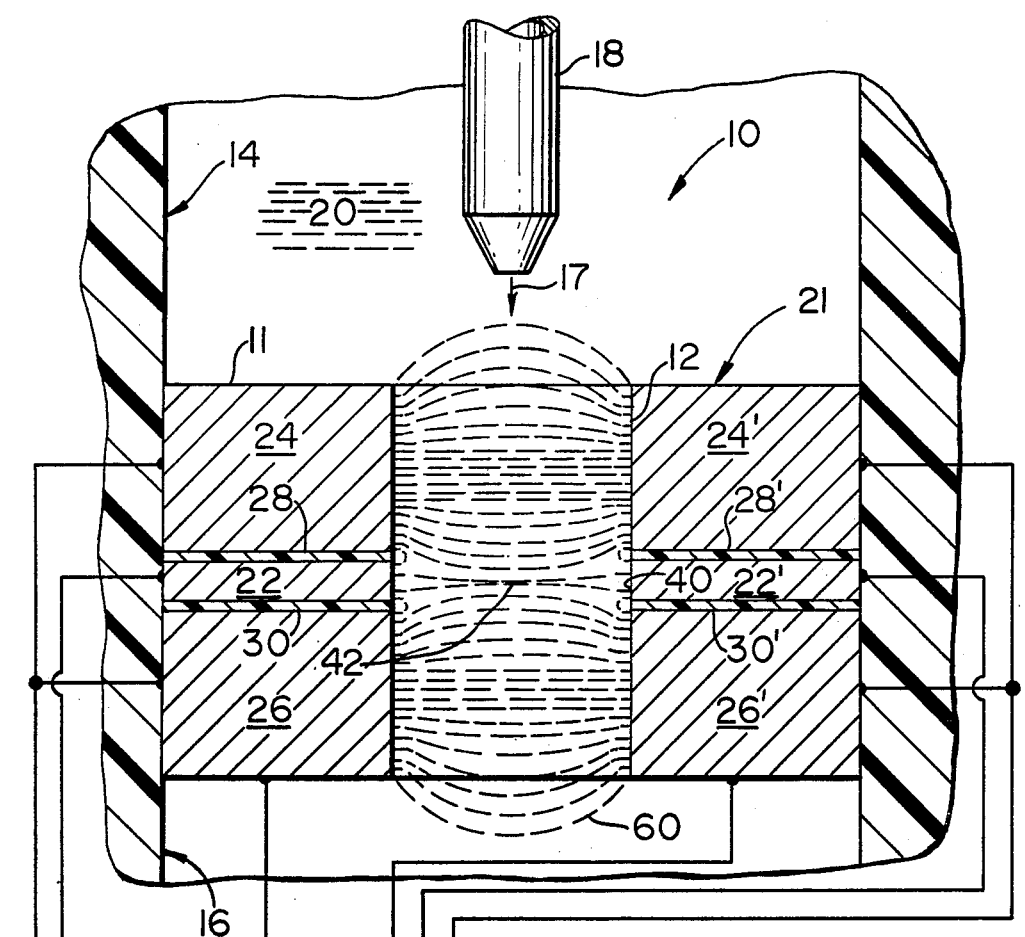
FIG. 1 shows a cross-sectional view of the sensing electrode arrangement, embodying the present invention, implemented in an aperture of a flow cell.

Referring to FIG. 1, a first embodiment of a flow cell 10 is disclosed having a dividing wall 11 with an aperture 12 formed therein. The aperture 12 terminates at its opposed ends in a pair of electrolyte-containing chambers 14 and 16. Preferably, but not necessarily a hydrodynamically focused fluid moving arrangement is used to pass a sample liquid suspension of particles, such as blood cells, through the aperture 12 in the direction of arrow 17. As is well known, an introduction tube 18 is used to introduce the sample suspension into a laminar liquid sheath 20 provided to the chamber 14, resulting in the sample suspension being a centered, focused stream as it passes through the aperture 12. As explained to this point, the flow cell 10 is of conventional design, as shown in U.S. Pat. No. 3,710,933 to Fulwyler et al.

Figure 2:
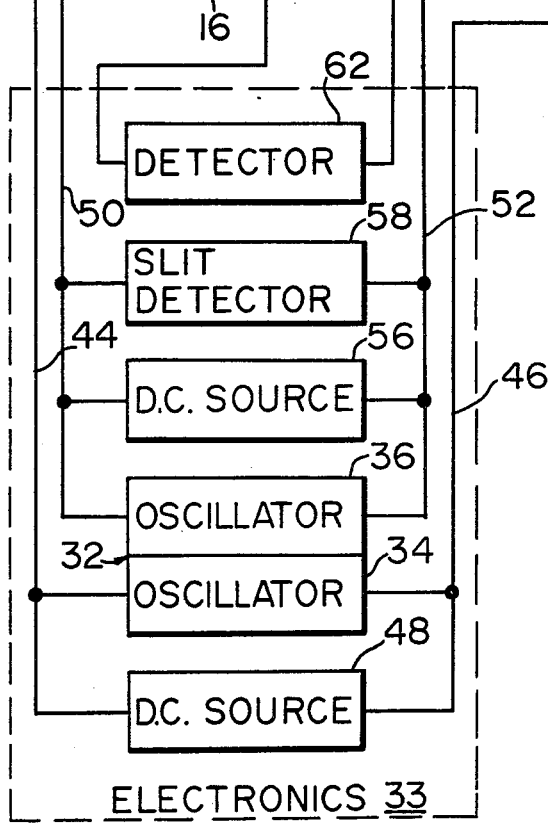
FIG. 2 shows a perspective view of the electrodes and the insulating layers therebetween as shown in FIG. 1, with the rest of the structure removed.
Figure 2:
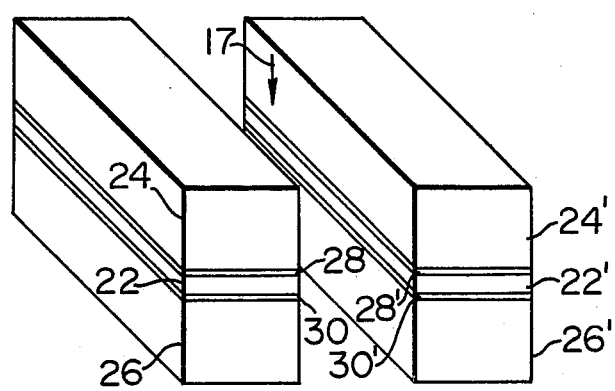

In an electrode sensing arrangement 21, a pair of electrically conductive, center electrode plates 22 and 22' are sandwiched between a first pair of electrically conductive outer electrode plates 24 and 24', respectively, on one side and a second pair of electrically conductive outer electrode plates 26 and 26', respectively, on the other side. The center plates 22 and 22' are separated and insulated from the adjacent outer plates by a first pair of relatively thin, electrically nonconductive layers 28 and 28' and a second pair of relatively thin, electrically nonconductive layers 30 and 30'. These plates are mounted in the electrically nonconductive dividing wall 11 so that the ends are preferably flush with the walls of the aperture 12. As better shown in FIG. 2, which illustrates in three dimensions the plates and layers, the plates and the insulating layers therebetween defining two walls of the aperture 12.

Depending upon the desired application, the plates can be energized by a low frequency source, i.e., including D.C., and/or a high frequency source normally with radio frequencies, as taught in the incorporated U.S. Pat. Nos. 3,502,973 and 3,502,974. In the embodiment of FIG. 1, the plates are shown energized by an RF current superimposed over a DC current, although either the RF or DC current alone can provide useful measurements.

Referring to FIG. 1, an alternating current energizing source 32 is provided with a pair of conventional phase-locked oscillators 34 and 36, with one being a reference oscillator and the other being a synchronized oscillator. In this manner, the oscillators 34 and 36 provide in-phase currents, normally in the radio frequency (RF) range, that can have different amplitudes. By way of conductors 44 and 46, the oscillator 34 is electrically coupled in parallel with the pair of outer plates 24, 24'; the pair of outer plates 26, 26'; and a DC current source 48, so as to create a RF current superimposed over a DC current for energizing the outer plates. Likewise, by way of conductors 50 and 52, the oscillator 36 is electrically coupled in parallel with the pair of center plates 22, 22'; a second DC current source 56; and slit detector circuitry 58. The detector circuitry 58 is of a design illustrated in said U.S. Pat. Nos. 3,502,973 and 3,502,974 and is electrically connected in parallel with the center plates 22, 22' so as to detect in a conventional manner changes in the electrical currents passing between the center plates, caused by the passage of the particles.

In the embodiment of FIG. 1, as previously explained, the RF currents produced by the oscillators 34 and 36 are in phase. On the other hand, the amplitude of the RF current produced by the oscillator 34 and the amplitude of the DC current produced by the first DC source 48 are greater than that of the RF current produced by the oscillator 36 and the amplitude of the DC current produced by the second DC source 56, respectively. As a result, the current lines 60 and electric field between the outer plates bulge outward toward the center plates, resulting in a narrowing of the current lines and electric field between the center plates. Additionally, there is current linkage between the center plates and the adjacent outer plates, so that the region of the center plates which has current lines traversing the aperture 12 is narrowed. The current lines 60 generally illustrate the boundaries of the sensing field 42 and the general direction of the electric field between the plates. However, for the sake of clarity, the spacing of the current lines do not correlate exactly to the electric field strength or intensity, in that there would be a substantially greater number of current lines between the outer plates, which cannot be readily illustrated. By virtue of this arrangement, a focused electrical field 40 is created between the center plates, which has a narrow center width that defines a sensing zone 42 for scanning the particles which pass therethrough. The width of the sensing zone 42 can be made relatively small fraction of the particle length, for example, 2 microns for a 10 micron particle.

Optionally, second detector circuitry 62 can be connected in electrical parallel with the outer plates 26, 26', as shown in FIG. 1 or outer plates 24, 24'. Alternatively, the detector circuitry 62 can be electrically coupled in parallel with both pairs of outer plates. Again, the detector circuitry 62 would take the form of that illustrated in the incorporated U.S. Pat. Nos. 3,602,973 and 3,502,974. In this manner, the field of the outer plates can also become sensing zones for the particles.

Depending upon the intended use of the flow cell 10, the detected particle pulses of the detector circuitry 58 can be processed and manipulated in many different, well known ways. For instance, with the D.C. particle pulses detected by the slit detector circuitry 58, the D.C. current lines must mostly pass around the outside of the cell; hence, the amplitude of the D.C. pulse represents the apparent volume of the cell. Additionally, if desired, the width of this D.C. particle pulse at a predetermined pulse threshold can be obtained and represents the length of the cell. By using the mathematical teachings of the incorporated U.S. patent application No. 4,298,836 the actual or true volume of each cell can be calculated.

With the R.F. particle pulses detected by the slit detector circuitry 58, the RF current lines pass through the cell, allowing for small sequential segments of the cell to be slit scanned by the slit sensing zone 52. This RF signal can be integrated, as taught by the integration of the optical signal in U.S. Pat. No. 3,864,571 to Stillman et al., to obtain the internal conductance of the cell. Moreover, the width of the pulse can be taken at different pulse thresholds to obtain the relative lengths and approximate relative sizes of the nucleus and surrounding cytoplasm, as taught by the optical length measurements in the previously mentioned U.S. Pat. No. 3,657,537.

By obtaining both the RF and DC particle pulses for a given particle, the apparent size measurement of the D.C. signal and the conductance measurement of the RF signal can be used to calculate the internal resistivity of the cell, which is also referred to as "opacity." If the cell's length measurement is also extracted from the DC particle pulse, the internal resistivity of the cell can be more accurately calculated by taking into account the particle's shape, as taught in the incorporated U.S. patent application No. 096,945. In addition, the internal conductivities of the cytoplasm and the nucleus can be calculated from the above described measured parameters, such parameters including the actual volume of the cell corrected for shape; the length of the cell, i.e., cytoplasm; the length of the nucleus; and the internal conductance of the cell as a function of time. With respect to the RF signal, the amplitude of the particle pulse at any point in time is a function of the volume of that segment of the cell which is in the sensing zone and the average conductivity of the cell's segment. In other words, the RF particle pulse represents the conductance of a continuously changing segment of the cell as a function of time. Consequently, the amount of change in the RF particle pulse when scanning the nucleus is a function of the size and conductivity of the nucleus, when the cell segments adjacent to those containing the nucleus are the same relative size. In this case, knowing the size of the nucleus, its conductivity can be calculated. By subtracting the volume and conductance of the nucleus from the cell's total volume and conductance, the conductivity of the cytoplasm can be calculated.

Instead of using the slit detector circuitry 58, the second detector circuit 62 can be optionally used to measure the cell's total conductance, if the RF signal is detected, and/or to measure the apparent D.C. volume, if the D.C. signal is detected. Since the sensing zone of the pair of plates 26, 26' is preferably several times greater in length than the cells, the detection of these signals are accomplished in a conventional manner. The detector 62 can be connected to either pair of the outer plates or both pairs in parallel. Likewise, the D.C. volume signal could be obtained in the conventional manner by having a pair of electrodes positioned in the vessels on either side of the aperture 12 to create a current therethrough.

In the preferred embodiment, as shown in FIG. 1, the center electric field 40 is reduced in only one dimension, this dimension being parallel to the direction of the sample flow. Since the width of the center field 40 can be made small, for instance, 2 microns, at the sensing zone 42, the width of the center plates 22, 22' can be made several hundreds of microns wide, and still have a current density in the sensing zone which is greater than that possible when passing the same current in the conventional manner through an aperture having a diameter of 50 to 100 microns. Moreover, the electrodes 22, 24, 26 can be spaced apart from the electrodes 22', 24', 26' by at least several hundreds of mirons. As a result of this field arrangement, the aperture 12 can be made sufficiently large that fabrication of the electrode arrangement can be readily accomplished.

Referring to FIG. 3, in the electrode sensing arrangement 21, the center electric field can be focused in two dimensions, with the added dimension being parallel to the center plates and perpendicular to the flow. More specifically, a pair of center electrode plates 68 and 68' are surrounded by outer electrodes 70 and 70', respectively. The electronics 33 remain the same as described in the embodiment of FIG. 1, with the exception of only needing one set of electrical connections to the outer electrodes 70 and 70'. Preferably, but not necessarily, the center electrode plates have a substantially greater width perpendicular to the flow than their depth parallel to the flow. By virtue of these dimensions, a sensing zone can be created with a cross section of, for instance, 2 microns by 20 microns. This provides a wide enough zone perpendicular to the flow to allow sufficient focusing of the particles therethrough; yet at the same time creates a sufficiently high current density that the aperture 12 can be enlarged, relative to that shown in FIG. 1, which in turn allows for easier fabrication of the electrode arrangement. In other words, the added focusing of the sensing field translates into a larger, easier to manufacture electrode arrangement. Alternatively, the outer electrodes 70 and 70' can each be broken into two pairs of opposed electrode plates, with each pair of opposed electrodes having a separate, in-phase energizing source. This would allow for easier adjustment of the focusing of the center field between the center electrodes.

FIG. 4 illustrates an alternative embodiment of the electrode sensing arrangement 21 wherein the two pairs of outer plates 24, 24' and 26, 26' are angularly positioned to have their outer ends tilted toward the center axis of the aperture 12 and their inner ends remaining positioned adjacent the center plates 22, 22'. Preferably, but not necessarily, the outer plates remain planar in configuration. The energizing source and detector arrangement for this embodiment can be the same as that shown with the embodiment of FIG. 1. However, as will be hereinafter explained, the bulging of the outer fields to create a narrow center field can be created solely by the angled electrodes, without a potential difference between the outer plates and the adjacent center plates. More specifically, if desired, the outer plates 24 and 26 and the center plate 22 can be held at one common D.C. potential and the outer plates 24' and 26' and the center plate 22' can be held at a different common D.C. potential. In this case, although two D.C. current sources are desirable, it is clear that in this embodiment a single D.C. source would be sufficient. Likewise, the oscillators 34 and 36 are not only in phase, but also can be adjusted, if desired, to generate radio frequency currents that have the same peak amplitudes. On the other hand, voltage differences between adjacent center and outer plates can be implemented, if desired.

In operation, the alternative embodiment of the sensing electrode arrangement 21 of FIG. 4 takes advantage of the fact that current lines 64 leave the surface of the plates at right angles, resulting in the electrical fields of the outer plates squeezing the electric field between the center plates into a narrow particle sensing zone 66. Moreover, this sensing zone 66 has a fairly uniform width over a large range of its center portion, making the detected signals less sensitive to particle trajectories and therefore resulting in less of a need for hydrodynamically focused particle flow.

FIG. 5 shows the electrode sensing arrangement 21 implemented on a surface 91 of a miroscope slide 92, which demonstrates the application of the invention in environments other than a flow cell, as shown in the earlier embodiments. The microscope slide 92 is implemented in a conventional flow cytometer arrangement illustrated in published Norwegian patent application No. 791,229 and in "Further Developments of a Microscope-Based Flow Cytometer: Light Scatter Detection and Excitation Intensity Compensation," by H. B. Steen, Cytometry, Vol. 1, (1980), pp. 28. In this system, a sheath tube 94 surrounds a sample introduction tube 95, so that the sample suspension, provided under positive pressure by a conduit 96 to the tube 95, is hydrodynamically focused by the sheath liquid, provided under positive pressure by a conduit 97 to the tube 94. A laminar liquid jet 98 exits from the sheath tube 94 into the atmosphere and is directed toward the surface 91 of the slide 92. When the jet 98 hits the microscope slide, the liquid spreads out into a thin layer 99, having a stable depth of, for example, 15 microns. In this thin layer 99, the particles remain confined to a narrow, stable section of the flow along a flow axis 100. The liquid layer is sucked up by an exit tube 101, which is coupled to a vacuum source (not shown).

As shown in FIG. 6, the electrode sensing arrangement 21 is implanted in the upper surface 91 of the slide 92 so that the tops of the electrodes 24, 24'; 22, 22'; and 26, 26' are preferably flush with the upper surface 91. Preferably, but not necessarily, the conductors 44, 46, 50 and 52 are connected to the electrodes through the underneath side of the slide 92. The remainder of the circuitry (not shown) is the same as shown in FIG. 1. Although the electrode arrangement 21 of the embodiment of FIG. 1 is implemented in the embodiment of FIGS. 5 and 6, the electrode arrangements of the embodiments of FIG. 4 can also be implemented in the slide arrangement of FIGS. 5 and 6, as shown in FIG. 6A. Moreover, the surface 91 can be any surface on a dielectric substrate with similar surface tension properties to glass and deviations from a strict planar configuration are possible.

Heretofore, in the prior art, a microscope 102, using a dark field arrangement, was incorporated so that its optical axis 104 would intersect the axis 100 of flow. In the present invention, the inclusion of this optical scanning of the particles is optional. Preferably, but not necessarily, the optical axis 104 is essentially coincident with the electrical sensing zone 42 or 66. The optical axis 104 amd the sensing zone 42 are positioned in relatively close proximity to the sheath tube 94, to obtain improved particle orientation. The electrodes can be, for example, etched, using conventional techniques for producing micro-circuits, into the top of the slide in positions a few 100 micrometers away from and on either side of the flow axis 100, so as to be totally covered by the thin liquid layer 99. Since the current lines must curve 90 degrees, after leaving or before entering the slide's surface, the electrodes are spaced from the flow axis 100 by a sufficient distance that the current density will be fairly uniform in the depth of the liquid layer 99. This spacing of the electrodes would normally cause a very broad, bulging electrical field relative to the flow axis 100, if the outer electrodes were not included. With the inclusion of the outer electrodes, the sensing field 42 is narrowed, allowing for the elimination of particle coincidence problems so as to give good throughput, for good current density, for good particle pulse resolution and, if desired, for electrical slit scanning. Due to the stability of the fluid depth of the liquid layer 99 and the capability of having a very small effective sensing zone, electronic noise is minimized.

The scope of the invention, as directed toward incorporating an electric sensing arrangement on a substrate, is substantially broader than the slit-like sensing zone 42 shown in FIG. 6, as will be shown in the subsequent embodiment. More specifically, as shown in FIG. 7, if the voltage of the center electrodes is held at the same level as the adjacent outer electrodes, a homogeneous field is achieved. Although electrical slit scanning of the cell cannot be achieved, the outer electrodes act to contain the electrical field 40 within reasonable width dimensions parallel to the flow axis 100. In other words, as described above, the field 40 is sufficiently narrowed to allow acceptable throughput of particles, while minimizing particle coincidence problems to acceptable levels. Typically, the width of the electric field 40 would be in excess of 100 microns. Moreover, although not particularly desirable, some outward bulging of the field 40 can be tolerable. In summary, one desirable feature of the electrode sensing arrangement according to the invention is that by focusing the electrical field 40 using adjacent electrical fields, the electrode 22 and 22' can be sufficiently spaced apart so as to assure a relatively uniform current density in the depth of the thin layer 99 in the sensing zone 42.

Since the width of the sensing zone 42 exceeds the particle length in FIG. 7, a length measurement for the cell can be obtained by using the teachings of U.S. Patent to Leary et al. More specifically, the pulse edge width of a particle pulse between two threshold values. established as constant fractions of the peak pulse amplitude, can be measured as an indication of the particle's length. Better signal resolution can be achieved in the present invention than in the Leary patent, in that the particle pulse includes the convolution of a substantially uniform electrical intensity profile, instead of the Gaussian electrical intensity profile of the Leary patent.

Another novel feature of the above described electrode sensing arrangement is that the electrode arrangement can be etched on the surface of the single slide or like substrate 91. In other words, the implementation of these electrode arrangements on a substrate frees the design of the constraints found in the prior art sensing aperture designs. More specifically, as illustrated in one possibility in FIG. 8, a multiple sensing zone arrangement is shown for accomplishing biological cell breakdown and for sensing the electrical characteristics of the cells before, during and after cell breakdown. Generally, the right-hand side of the electrode arrangement is the same as shown in FIG. 7 and includes the outer plates 26, 26' and center plates 22, 22'. The other set of outer plates, identified as 105 and 105', are angled inward toward the flow axis 100 at their end which is remotely disposed relative to the sensing zone 42. By virtue of this angled relationship, the current density increases as the cell passes through a breakdown sensing field, identified by numeral 107. Another electrical field is defined between closely spaced end plates 106, 106'. To illustrate one possible set of voltage conditions for the plates, the plates 26, 22, 105 and 106 are held to a first voltage V1 by a plurality of voltage sources 108, 110, 112 and 114, respectively. Likewise, the plates 26', 22', 105' and 106' are held at ground potential. The above voltage sources are DC, but RF currents could be superimposed thereover.

In the above described arrangement of FIG. 8, the volume of the cells would be sensed in a sensing field 116, electrical slit scanning can be accomplished in the sensing zone 42, the cell breakdown can be sensed in the sensing field 107, and the size of the cell after breakdown, which correlates with the internal conductance, can be measured in a sensing zone 118. The specific details for determining cell breakdown are known, as shown in U.S. Pat. No. 3,831,087 to Schulz et al. If the size measurement from the sensing field 118, which correlates with internal conductance, is divided by the volume signal from the sensing 116, a measurement of internal resistivity (opacity) is obtained. If desired, the plates 105 and 105' can be angled and curved to obtain an approximate linear ramp particle pulse signal as a particle, which does not experience breakdown, proceeds therethrough. As taught by U.S. Pat. No. 3,560,847, when a cell undergoes breakdown, there will be an abrupt change in the slope of the substantially linear output signal, which indicates at what voltage cell breakdown occurred. The electrodes 105 and 105' can be used by themselves, without the other electrodes, for cell breakdown analysis.

FIGS. 9 and 10 illustrate an alternative embodiment of the slide arrangement illustrated in FIGS. 5 through 8. In this alternative embodiment, a cover slide 120 is mounted over the slide 92 with a rubber gasket 122 positioned therebetween. The rubber gasket 122 has a central cutout portion 124 which allows for a chamber 126 to be defined between the two slides. The depth of this chamber 126 and the size of the electrode plates are exaggerated in these figures for the sake of illustration. The electrode plates are coupled by way of fine conductive wires 128 to electrode contacts 130. The sample introduction tube 95 and the sheath tube 94, along with the exit tube 101, are the same as shown in FIG. 5. The depth of the chamber 126 can be, for example, 130 microns, although smaller dimensions are possible.

If the electrode plates 26', 22' and 24' are mounted in the cover slide 120 and are cooperatively aligned above the electrode plates 26, 22 and 24, respectively, then essentially the same electrode arrangement as shown in FIG. 1 is achieved, without having the configuration of the aperture positioned between two fluid vessels. However, the difficulty of aligning the electrodes on two different substrates makes the design of FIGS. 5 and 6 substantially preferable from a fabrication standpoint. By using a single substrate, an exposed surface has the electrodes accurately completed therein and upon being implanted, there are no further alignment problems with the electrodes.

In summary, the sensing electrode arrangements embodying the present inventions can be implemented in an aperture arrangement, such as shown in FIGS. 1 through 4 wherein the aperture is mounted between two fluid vessels in the flow cell 10. Alternatively, in the preferred design the sensing electrode arrangements embodying the present inventions can also be implemented on the surface of a single substrate, such as the slide 92 in FIGS. 5 and 6, which eliminates the confines of the aperture design. Also, when implemented on the surface 91 of the slide 92, the analysis of the particles can be accomplished in a chamber 126 of a flow cell arrangement, such as shown in FIGS. 9 and 10. Although not shown, the electrodes also can be positioned across the chamber 126 from each other, returning to an electrode sensing arrangement such as illustrated in FIG. 1. In other words, the current lines will either leave the same surface, traverse the particle sensing zone, and return to the same surface, or, alternatively, the current lines will leave one surface, traverse the sensing zone and terminate on a second surface positioned on the opposed side of the sensing zone.

For the purposes of claiming the sensing arrangement embodying the invention, the term "plate" will be used in the claims to refer to the electrodes in the electrical field embodiments. However, it should be understood that only the end surface of each electrode, which is generally exposed to the suspension liquid and is operable for generating the electric fields, generally has a "plate-like" configuration. Although, these surfaces are generally planar, they can be curved. The remainder of the electrode embedded in the insulating material can vary in size, configuration and orientation. In the embodiments of FIGS. 1 through 4, the electrodes are typically embedded in a flow cell formed of plastic, while in the embodiments of FIGS. 5 through 10, the electrodes are typically embedded in substrates formed of glass or fused quartz.

With respect to the embodiments using electrical slit scanning, as shown in FIGS. 1, 4, 6 and 6A, the energizing sources 34 and 48 can be cooperatively varied in magnitude relative to the energizing sources 36 and 56 to progressively increase or decrease the width of the sensing zone 42 or 66 in a continuous or incremental manner. For example, the width of an initially narrow zone 42 or 66 can be increased by one micron increments while processing a given sample. Such control of the above stated energizing sources can be accomplished by electrically coupling the same through microprocessor-controlled potentiometers in a conventional manner, so as to provide a "programmed" sensing zone. In the above example, for fairly homogeneous particle populations, the pattern of resulting data obtained from the RF signal of slit detector 58 can give additional information on the population, such as shape and length information, since the output depends on the increasing slit thickness perceived by the particles. More specifically, the amplitudes of the RF particle pulses, after being normalized by the corresponding RF excitation current amplitudes, will continue to increase with the increasing width of the sensing zone until the width of the sensing zone exceeds the length of the cells. When the same approach is used on a non-homogeneous particle population of a variety of sizes, the ratio of the current normalized RF particle pulses to the size (volume) signals, obtained for example from detector 62, can provide shape information about the populations. Other uses for a slit electrical sensing field with a variable width will be apparent to those skilled in the art.

In all of the embodiments described herein, the multiple pairs of electrodes allow for tandem sensing fields in a manner which is simpler than in the conventional arrangements of mutliple apertures.

Although particular embodiments of the invention have been shown and described herein, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A particle analyzer apparatus comprising:
   means for providing a flow of a liquid suspension, having individual particles entrained therein, along a predetermined path;
   a first pair of metal plates positioned on opposed sides of said predetermined path;
   first energizing means for providing an electrical sensing field extending from one of said first plates through said liquid suspension to the other said first plate;
   field focusing means including a second pair of metal plates positioned on opposed sides of said predetermined path adjacent to one side of said first pair of plates and a third pair of metal plates positioned on opposed sides of said predetermined path adjacent to the opposed side of said first pair of plates;
   said field focusing means further including second energizing means for generating an electrical second field between said plates of said second pair and for generating an electrical third field between said plates of said third pair;
   said field focusing means further including field shaping means for angling at least a portion of said second and third fields in the direction of said sensing field to narrow the width of said sensing field along said predetermined path to a dimension less than the length of a given particle passing through said sensing field;
   detector means coupled to said first pair of plates for detecting particle pulses caused by particles passing through said sensing field.

2. The particle analyzing apparatus according to claim 1, wherein said particles comprise biological cells and said first energizing means and said second energizing means provide said fields at a radio frequency, whereby said sensing field scans a continuously changing portion of the given said particle so as not to scan the total particle at any one time.

3. The particle analyzing apparatus according to claim 1 or 2, wherein said first and second energizing means provides said fields with a zero to low frequency field, whereby said sensing field can provide size and length measurements of a given said particle.

4. The particle analyzer apparatus according to claim 1 wherein said field shaping means comprises said second energizing means generating a greater potential difference between said plates of said second and third pairs than said first energizing means generates between said plates of said first pair, whereby said second and third electrical fields bulge toward said sensing field to narrow said sensing field.

5. The particle analyzer apparatus according to claim 4, wherein said field shaping means further comprises said first and second energizing means providing said potential differences at relative voltage levels to create potential differences between said first plates and each adjacent said second and third plate that are substantially the same in absolute magnitude.

6. The particle analyzer apparatus according to claim 5, wherein said plates each have an exposed surface for electrical contact with said suspension liquid, said plates on one side of said predetermined path being disposed in spaced-apart coplanar relationship with each other and said plates on the other side of said predetermined path being disposed in spaced-apart, coplanar relationship with each other and in parallel relationship with said plates on said one side.

7. The particle analyzer apparatus according to claim 1, wherein said field shaping means comprising each of said plates having an exposed surface, said exposed surfaces of said second and third pairs of plates being disposed in angled relationship with respect to said exposed surfaces of said first plates so that each angled said plates has one end adjacent one of said plates of said first pair and the opposite end thereof angled inward toward said predetermined path; whereby said second and third fields, upon leaving said plates, are at least partially directed toward said sensing field so as to narrow the same.

8. The particle analyzer apparatus according to claim 1, wherein the said plates of said second and third pairs on each side of said predetermined path are joined to define two integral metal elements, one of said integral metal element being disposed in surrounding relationship to one of said first plates and the other said integral metal element being disposed in surrounding relationship to the other said first plate, whereby said sensing field is also narrowed in a direction perpendicular to said predetermined path.

9. The particle analyzer apparatus according to claim 1, wherein said means for providing a liquid suspension include a flow cell formed of an insulating material having a chamber formed therein for receiving said liquid suspension; said plates positioned on one side of said predetermined path being mounted in one side wall of said chamber and said plates positioned on the other side of said predetermined path being mounted in an opposed sidewall of said chamber.

10. The particle analyzer apparatus according to claim 1, wherein said means for providing a liquid suspension includes a substrate and means for moving said liquid suspension along the surface of said substrate and wherein said plates being mounted in said substrate.

11. The particle analyzer apparatus according to claim 1, wherein said particles comprise biological cells and one of said pair of electrodes has its electrodes tilted inward toward said predetermined path to create an increasing voltage gradient, with respect to particle movement along said predetermined path, for cell breakdown.

12. The particle analyzer apparatus according to claim 6 or 7, wherein said plates each have a substantially rectangular, substantially planar, surface exposed to said liquid suspension.

13. A particle analyzer apparatus comprising:
   a substrate;
   means for providing a flow of a liquid suspension, having individual particles entrained therein, on the surface of said substrate along a predetermined path;
   a first pair of electrodes mounted in said substrate on opposed sides of said predetermined path;
   first energizing means for providing an electrical sensing field and current extending from one of said electrodes through said liquid suspension to the other said electrode;
   field focusing means including a second pair of electrodes mounted in said substrate on opposed sides of said predetermined path adjacent said first pair of electrodes, a third pair of electrodes mounted in said substrate on opposed sides of said predetermined path adjacent said first pair of electrodes, said second pair of electrodes being positioned on one side of said first pair of electrodes and said third pair of electrodes being positioned on the other side of said first pair of electrodes;

said field focusing means further including second energizing means for generating an electrical second field and current between said electrodes of said second pair and for generating an electrical third field and current between said electrodes of said third pair;

detector means coupled to said first pair of electrodes for detecting particle pulses caused by particles passing caused by particles passing through said sensing field;

whereby said second and third electric fields confine said sensing field to a desired width along said predetermined path.

14. The particle analyzer apparatus according to claim 13, wherein said particles comprise biological cells and said first energizing means and said second energizing means provides said electrical fields and currents at a radio frequency, whereby said sensing field scans the internal constituents of the given said particle.

15. The particle analyzing apparatus according to claim 13 or 14, wherein said first and second energizing means provides said electrical fields and currents with a zero or low frequency, whereby said electrical sensing field provides size measurements of a given said particle.

16. The particle analyzer apparatus according to claim 14, wherein said field focusing means further includes field shaping means for angling at least a portion of said second and third fields in the direction of said sensing field to narrow the width of said sensing field along said predetermined path to a dimension less than the length of a given particle passing through said sensing field.

17. The particle analyzer apparatus according to claim 16, wherein said field shaping means comprises said second energizing means generating a greater potential difference between said electrodes of said second and third pairs than said first energizing means generates between said electrodes of said first pair, whereby said second and third electrical fields to narrow said sensing field.

18. The particle analyzer apparatus according to claim 17, wherein said field shaping means further comprises said first and second energizing means providing said potential differences at voltage levels to create absolute magnitude potential differences between said first electrodes and each adjacent said second and third electrodes that are substantially the same in absolute magnitude.

19. The particle analyzer apparatus according to claim 13, wherein said electrodes each have an exposed surface for electrical contact with said suspension surface, said electrodes on one side of said predetermined path being disposed in spaced-apart coplanar relationship with each other and said electrodes on the other side of said predetermined path being disposed in space-apart, coplanar relationship with each other and in parallel relationship with said electrodes on said opposite side.

20. The particle analyzer apparatus according to claim 16, wherein said field shaping means comprises each of said electrodes having an exposed surface, said exposed surfaces of said second and third pairs of electrodes being disposed in angled relationship with respect to said exposed surfaces of said first electrodes so that each angled said electrode has one end adjacent one of said electrodes of said first pair and the opposite end thereof angled inward toward said predetermined path; whereby said second and third fields, upon leaving said electrodes, are at least partially directed toward said sensing field so as to narrow the same.

21. The particle analyzer apparatus according to claim 13, wherein said particles comprise biological cells and one of said pair of electrodes has its electrodes tilted inward toward said predetermined path to create an increasing voltage gradient, with respect to particle movement along said predetermined path, for cell breakdown.

22. The particle analyzer apparatus according to claim 13 wherein said electric sensing field has a width along said predetermined path that is greater than the lengths of said particles.

23. The particle analyzer apparatus according to claim 1 or 16, further including means for changing the width of said electrical sensing field while the liquid suspension is passing therethrough.

24. The particle analyzing apparatus according to any one of claims 4, 7, 16 or 20 wherein said particles comprise biological cells and said first energizing means and said second energizing means provide said fields at a radio frequency, whereby said sensing field scans a continuously changing portion of the given said particle so as not to scan the total particle at any one time.

25. A particle analyzer apparatus comprising:
first means for providing a flow of a liquid suspension, having individual particles entrained therein, along a predetermined path;
second means for providing a narrow electrical field across said predetermined path, said electrical field having a width along said predetermined path that is less than the length of a given particle passing through said electrical field; and
third means, electrically coupled to said second means, for detecting particle pulses caused by particles passing through said electrical field.

26. The particle analyzer apparatus according to claim 25, wherein said second means provides said electrical field with a high frequency for causing said electrical field to pass through said particles, whereby continually differing, narrow elongated portions of said given particle are examined.

27. The particle analyzer apparatus according to claim 25 or 26, wherein said first means includes a substrate and means for providing said flow of said liquid suspension in a relatively thin layer on the surface of said substrate.

28. The particle analyzer apparatus according to claim 25 or 26, wherein said first means includes focusing means for focusing said electric field to said width that is less than the length of said given particle.

* * * * *

UNITED STATES PATENT AND TRADEMARK OFFICE
CERTIFICATE OF CORRECTION

PATENT NO. : 4,420,720

DATED : December 13, 1983

INVENTOR(S) : WILLIAM A. NEWTON et al

It is certified that error appears in the above—identified patent and that said Letters Patent is hereby corrected as shown below:

Column 1, line 57, change "neglible" to --negligible--.
Column 3, line 40, change "ech" to --each--.
Column 6, line 63, delete "application".
Column 7, line 1, change "52" to --42--; line 15, change "opacity." to --"opacity".--; line 20, delete "application".
Column 8, line 1, change "mirons" to --microns--.
Column 9, line 5, change "miroscope" to --microscope--; line 13, change "Compensation," to --Compensation",--.
Column 10, line 36, change "values." to --values,--.
Column 11, line 15, after "sensing", insert --field--.
Column 12, line 60, change "mutliple" to --multiple--.
Column 14, line 2, change "comprising" to --comprises--; line 26, change "include" to --includes--.
Column 15, line 11, delete "caused by particles passing"; line 54, change "13" to --18--.

Signed and Sealed this

Twenty-ninth Day of May 1984

[SEAL]

Attest:

GERALD J. MOSSINGHOFF

Attesting Officer

Commissioner of Patents and Trademarks